United States Patent [19]

Böck et al.

[11] Patent Number: 5,395,927
[45] Date of Patent: Mar. 7, 1995

[54] DNA-FRAGMENT HAVING THE CYCLODEXTRIN GLYCOSYLTRANFERASE GENE

[75] Inventors: August Böck, Geltendorf; Florian Binder, Munich; Frank Müller, Höhenkirchen, all of Germany

[73] Assignee: Consortium für elektrochemische Industries GmbH, Munich, Germany

[21] Appl. No.: 450,126

[22] Filed: Nov. 27, 1989

Related U.S. Application Data

[63] Continuation of Ser. No. 923,128, Oct. 24, 1986, abandoned.

[30] Foreign Application Priority Data

Oct. 29, 1985 [DE]  Germany .................. 35 38 433.6

[51] Int. Cl.$^6$ ............................................. C07H 21/04
[52] U.S. Cl. ........................................ 536/23.2; 435/6; 435/15; 435/91.1; 536/23.1; 536/24.1; 536/24.32; 935/9; 935/14; 935/19
[58] Field of Search ............... 435/15, 97, 103, 193, 435/275, 837, 852, 69.1, 91.1, 69.8, 172.3; 536/26, 27, 28, 22.1, 23.1, 23.2, 24.1, 24.31–24.33; 935/9, 14, 19, 29, 48, 72, 74, 78

[56] References Cited

U.S. PATENT DOCUMENTS 4,667,025  5/1987  Miyoshi et al. ................ 536/27

FOREIGN PATENT DOCUMENTS 2213340  8/1974  France .
2574081  6/1986  France .

OTHER PUBLICATIONS

*Nucleic acid hybridisation*, (Eds. Hames et al., IRL Press, Wash. D.C., 1985) p. 80.
New England Biolabs Catalog (1986/1987) (publ. by New England Biolabs, Beverly, Mass., USA) p. 60.
*Bethesda Research Laboratories, Catalogue & Reference Guide* (Bethesda Research Labs., Gaithersburg, Md. USA, 1985) p. 52.

Lehringer, (1970) *Biotechnology* (Worth Publishers Inc., New York, N.Y.), p. 228.
Binder et al. (1986) Gene, vol. 47, pp. 269–277.
Yang et al. (1983) Nucleic Acids Res., vol. 11, No. 2, pp. 237–249.
Sigma Catalog (1990), Sigma Chemical Co., St. Louis, Mo.
Kobayashi et al., Carbohydrate Rresearch, 61 (1978), pp. 229–238, "Purification and Some Properties of Bacillus Macerans Cycloamylose (Cyclodextrin) Glucanotransferase".
Hans Bender, Arch. Microbiol. 111, S. 271∝282, (1977), "Cyclodextrin-Glucanotransferase von Klebsiella pneumoniae".
Boyer et al., J. Mol. Biol. (1969), 41, pp. 459–472, "A Complementation Analysis of the Restriction and Modification of DNA in Escherichia coli".
J. Gregor Sutcliffe, Nucleic Acids Research, vol. 5, No. 8, Aug. 1978, "pBR322 Restriction Map Derived from the DNA Sequence: Accurate DNA Size Markers up to 4361 Nucleotide Pairs Long".
Hennecke et al., Gene, 19 (1982), pp. 231–234, "A Novel Cloning Vector for the Direct Selection of Recombinant DNA in E. coli".
MacNeil et al., Journal of Bacteriology, vol. 136, No. 1, Oct. 1978, pp. 253–266, "Fine-Structure Mapping and Complementation Analysis of nif (Nitrogen Fixation) Genes in Klebsiella pneumoniae".
Bender, Arch. Microbiol. 111, 271–282 (1977).
Bender, Arch. Microbiol. 113, 49–56 (1977).
Horikoshi and Akiba, (1982) Alkalophilic Microorganisms, excerpt, pp. 10, 11 DSM, Catalogue of Strains 1989, p. 24.

(List continued on next page.)

Primary Examiner—Margaret Parr
Assistant Examiner—Ardin H. Marschel
Attorney, Agent, or Firm—Collard & Roe

[57]  ABSTRACT

The invention relates to DNA fragments having the cyclodextrin glycosyltransferase structural gene, to vectors and microorganisms for expression and to a preparation process for the same.

5 Claims, 1 Drawing Sheet

OTHER PUBLICATIONS

Data for Biochemical Research, p. 288, by Dawson et al. (1986).

"Cloning and Sequencing of a Moraxella bovis Pilin Gene," Marrs et al., *J. of Bacteriology*, Jul. 1985, p. 132.

"Molecular Clonging of nif DNA from Azotobacter vinelandii," Bishop et al., *J. of Bacteriology*, Apr. 1985, p. 21.

De Baer et al., Proc. Nat Acad Sci. (1983) vol. 80 pp. 21–25.

Takano et al. Chemical Abstracts, vol. 105 (21), Nov. 1986, p. 595.

Takano et al., Journal of Bacteriology, vol. 166(3), Jun. 1986, pp. 1118–1122.

Takano et al., Chemical Abstracts, vol. 107(9), Aug. 31, 1987, p. 193.

Takano Patent Abstracts of Japan, vol. 10 (321) (C-382) (2377) Oct. 31, 1986.

R. W. Old et al.: "Principles of gene manipulation", 3th edition, 1985 pp. 138–140.

Laszlo et al. Starch–Starke, vol. 33 (8), Aug. 1981, pp. 281–283.

T. Maniatis et al.: "Molecular cloning: A laboratory manual" 1982, pp. 295–306.

Takizawa et al. Appl. and Envir. Microbiol. (1985) vol. 49 pp. 294–298.

Bender Arch. Microbiol. (1977) 111 (3) pp. 271–282

Takano et al. J. of Bacteriol. (1986) vol. 166 3 pp. 1118–1122.

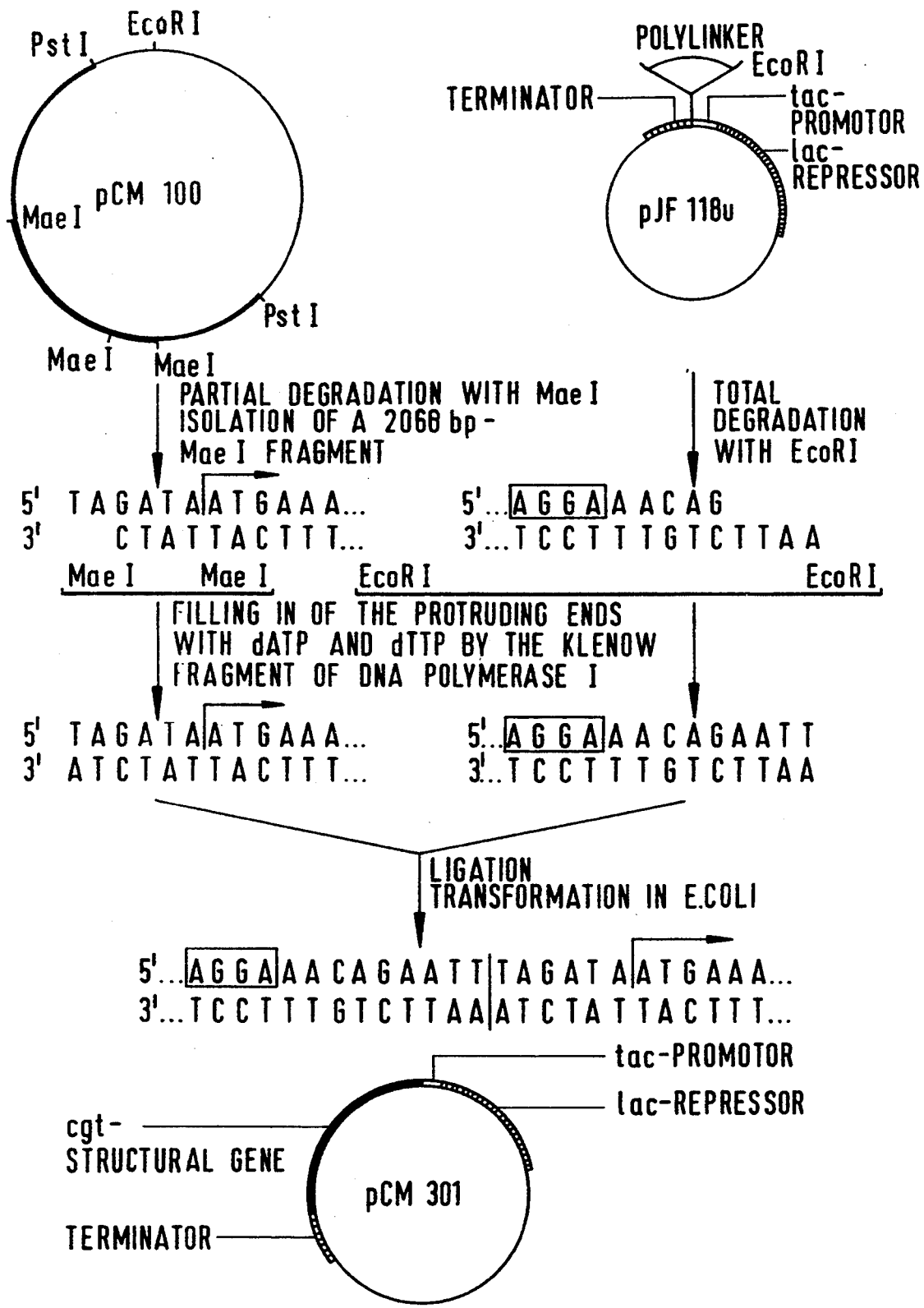

DNA-FRAGMENT HAVING THE CYCLODEXTRIN GLYCOSYLTRANFERASE GENE

CROSS REFERENCE TO RELATED APPLICATION

This is a continuation of prior co-pending U.S. patent application Ser. No. 923,128 filed Oct. 24, 1986, and now abandoned.

This invention relates to a DNA fragment having the cyclodextrin glycosyltransferase structural gene, an expression vector, microorganisms for expression, and a preparation process.

Cyclodextrins are starch degradation products which result from the hydrolysis of starch by the enzyme cyclodextrin glycosyltransferase (CGT; E.C. 2.4.1.19). Cyclodextrin glycosyltransferases have hitherto been described for *Bacillus macerans* (for example, ATCC 8514), *Bacillus megaterium* (*Carbohydr. Res.*, 61 (1978) 229–238), alkalophilic Bacillus species (for example, ATCC 21594, 21595, 21783, 31006 and 31007) and for *Klebsiella pneumoniae* (for example, M5al; *Arch. Microbiol.*, 111 (1977) 271–282).

CGT from *Klebsiella pneumoniae* (for example, M5 al) is a monomeric polypeptide with a molecular weight of about 69,000 D. This polypeptide is synthesized by the bacterium as a precursor protein with a molecular weight of about 73,000D and, with elimination of a signal peptide of 30 amino acid residues, is released from the cell into the medium.

The enzyme synthesis is strictly regulated, in particular, it is subject to catabolite repression and to induction. This means that the enzyme is synthesized only if, for example, *Klebsiella pneumoniae* M5al grows on starch, cyclodextrins or maltooligosaccharides. If the bacterium grows on other carbon sources then enzyme synthesis is suppressed or not induced. Since there is no question of using maltooligosaccharides and cyclodextrins, for reasons of cost, satisfactory yields of CGT are obtained, but only by continuous culturing of *Klebsiella pneumoniae* M5al. Continuous culturing is necessary to limit the addition of starch as the carbon source. Since, by reason of its properties (poor solubility, high viscosity of the solution), starch is a substrate which is difficult to manipulate, considerable problems arise in the fermentation. Another critical factor is the use of CGT from the potentially pathogenic bacterium *Klebsiella pneumoniae*, especially in the foodstuff sector and in the pharmaceutical sector.

Thus, an object of the present invention is to make available live material with which one or more of the following contributory objects can be achieved:

the amount of CGT formed should be as large as possible;

the regulation of the enzyme synthesis should be modified so that it is easy to carry out, that is to say makes possible fermentation with problem-free carbon sources; and there should be provision of non-pathogenic microorganisms, in particular, bacteria, which produce CGT, and these microorganisms ought to make the enzyme amenable to use in the foodstuff sector and pharmaceutical sector as well.

The foregoing and related objects are attained by the present invention which provides DNA fragments which embrace the cyclodextrin glycosyltransferase structural gene ("CGT structural gene") as well as of DNA fragments whose single strands are able, at not below 20° C., and in particular at a concentration of 1 M NaCl and a temperature not below 25° C., to hybridize with those of the DNA fragments which embrace the CGT structural gene. The DNA fragments may lack the signal or leader coding regions for their expression.

The invention, more particularly, relates to DNA fragments which are of this type and have about 2,068 basepairs (bp), it being possible to cut, using the restriction enzyme MaeI, these DNA fragments out of DNA structures of microorganisms which produce CGT. Examples of species and strains of microorganisms of this type have been mentioned above. However, the person skilled in the art can also isolate suitable strains from soil samples.

The invention furthermore relates to:

expression vectors which embrace the DNA fragments;

tac promoter plasmids such as pKK223-3 and pJF118u;

Lambda-$p_L$ promoter plasmids such as pPL-Lambda; and trp promoter plasmids such as pDR720; each of which embrace the above-mentioned DNA fragments;

non-pathogenic microorganisms which embrace the expression vectors and can be cultivated industrially;

non-pathogenic bacteria which can be cultivated industrially, as example of microorganisms which embrace the expression vectors; and microorganisms of this type, especially bacteria of this type, which are approved for addition to foodstuffs.

Finally, according to the invention there is provided a process for the preparation of the said DNA fragments, of the expression vectors and of the microorganisms, in which:

(a) starting, from microorganisms which produce CGT, their genome is isolated and randomly fragmented;

(b) the genome fragments which have been obtained are inserted in vectors, the recombinant vectors are transferred into microorganisms which can be cultivated, screening is carried out for those clones which produce CGT, and these clones are isolated;

(c) and/or the recombinant vectors are isolated from the CGT-producing clones;

(d) and/or DNA fragments which embrace the CGT structural gene are cut out of the recombinant vectors;

(e) and/or the DNA fragments which have been cut out are inserted in expression vectors;

(f) and/or the recombinant expression vectors which have been obtained are transferred into non-pathogenic microorganisms which can be cultivated industrially.

Thus, according to the invention, recombinant DNA methods are used to transfer into a vector the gene which is responsible for coding for CGT. It is possible by the process, according to the invention, to obtain a high copy number of the gene and —by specific modification of the regulation of gene expression— to obtain the enzyme in high concentration. Accordingly, the culture supernatant or the crude cell extract may be usable directly or in an immobilized form for the formation of cyclodextrins.

Hence, stage (a) starts with microorganism species or strains which produce CGT, for example *Klebsiella pneumoniae* M5al. Thus, for example, with *Klebsiella pneumoniae* M5al it is possible to isolate the entire DNA which contains the gene for CGT. This can take place by culturing the strain in a suitable nutrient medium at 30° to 37° C., followed by lysis of the cells and purification of DNA by density gradient centrifugation and dialysis.

Thus, if *Klebsiella pneumoniae* M5al is used, for example, it is possible to isolate its entire DNA, as well as the DNA of the vector, which is to be inserted by incubation with the restriction endonuclease PstI (E.C.3.1.23.31) at about 37° C. until the DNA molecules have been completely cleaved. The endonuclease can then be deactivated. By gel electrophoresis, one can fractionate the resulting fragments of the entire DNA from *Klebsiella pneumoniae* M5al and isolate fragments having a length of about 5,400 base-pairs.

Recombination of the resulting DNA fragments, which are about 5,400 base-pairs in length, with the cleaved vector can be effected by mixing the fragments and incubating the solution with a suitable DNA ligase, preferably with the DNA ligase from the phage T4 (E.C.6.5.1.1.). The ligation is preferably carried out in the presence of ATP, of a sulfhydryl compound and magnesium ions. So-called competent strains, which have the ability to take up DNA, are transformed in a known manner with the recombinant DNA which has been obtained.

For the present invention, one could employ as transformable strains, the strains which are known for this purpose. These are, in particular, strains of *E. coli, Klebsiella pneumoniae, Bacillus subtilis* and *Saccharomyces cerevisiae.* Use is made in this first transformation step of strains of *E. coli,* such as, HB101 (DSM 1452; *J. Mol. Biol.,* 41, (1966) 459–472).

The person skilled in the art is familiar with the choice of vectors suitable for the cells which are used and are to be transformed. When strains of *E. coli* or *Klebsiella pneumoniae* are used, examples of plasmids suitable for the first recombination, step (b), in the process according to the invention are pBR322 (*Nucl. Acids Res.,* 5, (1978) 2721–2728) and pHE3 (Gene, 19, (1982) 231–234).

In order, after the first transformation step, in the process according to the invention, to find those cells which contain the vector carrying the gene for CGT, one may culture the transformed cells on a minimal medium which contains starch as a carbon source, the necessary salts and supplements, an antibiotic for selection of the vector, and amylopectin azure as indicator for starch degradation. The cells which contain the vector carrying the gene for CGT form a colorless degradation zone and are isolated.

For a second recombination step in the process according to the invention, it is possible in stages (c) and (d) to obtain the plasmid DNA from the isolated cells by known methods, and to cut out, with a restriction endonuclease, DNA fragments which embrace the CGT structural gene. A preferred restriction enzyme is MaeI (E.C.3.1.23.—), with which partial cleavage is carried out at, for example, about 45° C. The resulting fragments of the plasmid DNA containing the gene for CGT are fractionated by, for example, gel electrophoresis. If cutting has been carried out with the restriction endonuclease MaeI, then a fragment which has a length of about 2,068 base-pairs and which carries the structural gene for CGT, but not the signal structures for its expression, is isolated. The 5' protruding ends of the fragment can be filled in with deoxy-ATP and deoxy-TTP by incubation with a suitable DNA polymerase so that blunt ends are produced. The Klenow fragment of DNA polymerase I (E.C.2.7.7.7) is preferably used.

In another embodiment of the claimed process, however, it is also possible in stage (d) to linearize, with a suitable restriction endonuclease, the vector obtained in the first transformation step, and then to incubate it with an exonuclease, for example with Ba131, until there is produced, by stepwise elimination of nucleotides from the ends, a fragment which contains the gene for CGT but preferably not its signal structures. Protruding ends of the fragment can be filled in with deoxynucleotides using a DNA polymerase so that blunt ends are produced.

It is possible for the second recombination step in the process according to the invention, namely stage (e), to use so-called expression vectors which contain readily controllable regulatory sequences and effect high expression of the recombined gene. It is possible, for example, to use for the transformation of strains of *E. coli* and *Klebsiella pneumoniae* tac promoter plasmids such as pKK223-2 (commercially available) and pJF118u; pJF118u corresponds to PKK223-3 with the exceptions that a 0.546 kb BamHI-XmaIII fragment has been deleted and a 1.26 kb fragment with the lactose repressor gene (LacI$^q$) has been inserted. However, it is also possible to use other plasmids, for example, Lambda-p$_L$ promoter plasmids such as pPL-Lambda (commercially available), and trp promoter plasmids such as pDR720 (commercially available).

The vector DNA is cleaved with a suitable restriction endonuclease. The restriction endonuclease is then inactivated. Protruding ends can be filled in with deoxynucleotides using a suitable DNA polymerase, or can be cleaved off, so that blunt ends are produced. It is possible and preferable to use for this purpose the Klenow fragment of DNA polymerase I or the DNA polymerase of the phage T4.

Recombination of the DNA fragment, which embraces the CGT structural gene with the vector DNA, can be achieved by mixing the fragments and incubating the solution with a suitable DNA ligase, preferably with DNA ligase from the phage T4 (E.C.6.5.1.1.). Ligation is advantageously carried out in the presence of ATP, of a sulfhydryl compound and magnesium ions.

It is possible in stage (f) of the process according to the invention to transform, in a known manner, the resulting recombinant DNA into so-called competent strains which have the ability to take up DNA. In this second transformation step in the process, the selection of the transformable cells is based on other desired properties of these cells, such as, for example, properties of growth, of pathogenicity and of the ability to export proteins. Strains of *E. coli,* such as, HB101 and JM 105 (commercially available), and *Klebsiella pneumoniae,* such as, UN1290 (*J. Bacteriol.* 136, (1978) 253–266) are preferably used. However, it is also possible to use transformable cells of other strains such as, for example, of *Saccharomyces cerevisiae* and *Bacillus subtilis.*

After the transformation it is possible to culture those cells which contain plasmids on a nutrient medium which contains an antibiotic. Specifically, one could set up parallel cultures of those cells which contain a plasmid, on the one hand, on a minimal medium which contains glucose as a carbon source, the necessary salts and supplements, an antibiotic for selection of the vector, and amylopectin azure as indicator, for starch degradation. On the other hand, on the same minimal medium also contains, in addition, an inducer, for example, isopropyl β-D-thiogalactoside, in the case of the vector pKK223-3. Those cells which form a colorless degradation zone with the inducer, and thus are obviously under the control of the promoter, are isolated. They have the structural gene for CGT, which is under the control of the expression promoter. This is the tac promoter in the case of the vector pKK223-3.

In stages (d) and (e) of the process according to the invention, it is advantageous for the second recombination step to use the restriction endonuclease MaeI for the partial cleavage of the plasmid DNA resulting after the first transformation. This is because the latter restriction enzyme effects cleavage at advantageous sites on the DNA, namely between the ribosome binding site and the site where translation commences, on the one hand, and downstream of the termination signals for transcription and translation of the DNA sequence containing the gene for CGT on the other hand.

It is emphasized once more that the invention embraces not only the DNA fragments which embrace the CGT structural gene, and can be obtained by the process according to the invention, but also DNA fragments whose single strands can hybridize with those of the DNA fragments having the CGT structural gene. "Hybridizable" DNA fragments of this type can result from, for example, modification of the DNA fragments which embrace the CGT structural gene. Extension of the invention to include these "hybridizable" DNA fragments also takes into account the fact that the structural genes of the microorganisms which produce CGT may differ. Modified DNA fragments are of interest as long as expression of enzymes having CGT activity is possible with their aid.

The microorganism *Klebsiella pneumoniae* M5al has been deposited under the number DSM 3539 at the Deutsche Sammlung von Mikroorganismen (German Microorganism Collection) in D-3400 Göttingen, Grisebachstrasse 8.

BRIEF DESCRIPTION OF THE DRAWING

FIG. 1. The invention is explained in detail hereinafter by a diagram (FIG. 1) and an example. It is to be understood that the drawing and example are to be used for the purpose of illustration only, and not as a definition of the limits of the invention.

EXAMPLE

The following process steps are used to prepare from the entire DNA of the strain *Klebsiella pneumoniae* M5al, which carries the gene for cyclodextrin glycosyltransferase, new strains of high cyclodextrin glycosyltransferase productivity:

(1) Isolation of the entire DNA from *Klebsiella pneumoniae* M5al which contains the genetic information for cyclodextrin glycosyltransferase.

The strain *Klebsiella pneumoniae* M5al is cultured to the end of the exponential phase in 200 ml of nutrient broth which contains 1% tryptone, 0.5% yeast extract and 1% NaCl at 37° C. After harvesting, the cells are taken up in 2.5 ml of TES buffer (50 mM Tris/HCl pH 7.5; 50 mM NaCl; 5 mM EDTA), which contains sucrose and 5 mg Lysozyme, and incubated at 37° C. for 10 minutes. After addition of 2.5 ml of lysis solution (10 mM Tris/HCl pH 7.5; 1 mM EDTA; 0.1% TRITON X100, which is Polyoxyethylene (9-10) p-t-octylphenol, proteinase K is added to the mixture to a final concentration of 0.1 mg/ml, and the mixture is incubated at 37° C. for 30 minutes. The DNA is isolated from the lysate by cesium chloride density gradient centrifugation and dialysis against buffer (10 mM Tris/HCl pH 8.0; 1 mM EDTA).

(2) Isolation of the vector DNA.

DNA of the plasmid pBR322, which carries ampicillin and tetracycline genes as markers, is used for cloning the gene for cyclodextrin glycosyltransferase. It is isolated in the following manner:

An *E. coli* strain which contains the plasmid pBR322 is cultured to the end of the exponential growth phase in 0.5 ml of nutrient broth as in (1) at 37° C., with shaking. After addition of 150 μg/ml chloramphenicol, shaking is continued at the same temperature for 15 hours. The bacterial cells are then obtained, lyzed with lysozyme and a non-ionic detergent, and the lysate is centrifuged at 48,000 g for 30 minutes. The plasmid DNA is obtained from the supernatant by two cesium chloride equilibrium density gradient centrifugations and dialyses against buffer as in (1).

(3) Insertion of the gene, coding for cyclodextrin glycosyl-transferase, from Klebsiella pneumoniae M5al into the vector.

10 μg of the entire DNA from *Klebsiella pneumoniae* M5al and 1 μg of the vector DNA are treated with the restriction endonuclease PstI for two hours, in order to cleave the DNA each case. The entire DNA from *Klebsiella pneumoniae* is then molecules completely, and then heated at 68° C. for 10 minutes in fractionated by electrophoresis in a 0.6% agarose gel. The fragments with a size of about 5,400 base-pairs are cut out and, after phenol extraction and ethanol precipitation, dissolved in water.

The solution of the fragments of the entire DNA of *Klebsiella pneumoniae* M5al which have thus been obtained is mixed with the solution of the cleaved pBR322 vector DNA and after addition of ATP, dithiothreitol and magnesium chloride, the mixture is incubated with the DNA ligase of the phage T4 at 17° C. for 16 hours. The resulting solution contains the recombinant DNA.

(4) Genetic transformation of *E. coli* bacteria with recombinant DNA which contains the genetic information for cyclodextrin glycosyltransferase.

The *E. coli* strain HB101 is cultured to the end of the exponential phase by shaking in 20 ml of nutrient broth as in (1) at 37° C. The cells are obtained, suspended in 10 ml of ice-cold 50 mM calcium chloride solution, and incubated in an ice-bath for 30 minutes. The cells are subsequently obtained by centrifugation and then suspended in 2 ml of ice-cold 50 mM calcium chloride solution. 0.2 ml of the suspension is mixed with the solution of recombinant DNA from stage (3), and incubated in an ice-bath for 30 minutes and then at 43° C. for 5 minutes. The cells are inoculated into nutrient broth as in (1) and shaken at 37° C. for 45 minutes. The cells are then plated out in portions on agar plates which contain 7.1 g of $Na_2HPO_4$, 13.6 g of $KH_2PO_4$, 15 mg of $CaCl_2$, 0.25 g of $MgSO_4$, 1.6 g of $(NH_4)_2SO_4$, 5 mg of thiamine, 40 mg of proline, 40 mg of leucine, 20 mg of tetracycline, 5 g of starch, 5 g of amylopectin azure and 15 g of agar per liter. The plates are incubated at 37° C. After incubation for 3 days, colonies appear on the plates, some of which are surrounded by colorless zones on the plates which are otherwise deep blue. The latter colonies are removed, purified and isolated. Each of the colonies thus obtained is able to degrade starch and is, at the same time, tetracycline-resistant. Thus, its properties differ from those of the strain used as host organism. This means that the isolated cells contain the plasmid pBR322 which carries the PstI fragment from *Klebsiella pneumoniae* M5al having the cyclodextrin glycosyltransferase gene.

The plasmid DNA is isolated from one of the resulting colonies by the process described in (2). Two fragments are found after treatment with restriction endonuclease PstI and analysis by electrophoresis in an agarose gel. This plasmid is called pCM100. Bacteria which carry this plasmid can degrade starch and they produce cyclodextrin glycosyltransferase.

(5) 10 μg of the DNA of the plasmid pCM100 from HB101 are treated with the restriction endonuclease MaeI at 45° C. so that the DNA molecules are partially cleaved. The DNA fragments are fractionated by electrophoresis in a 1% agarose gel. The fragment with a length of 2,068 base-pairs is cut out and isolated as in (3). The 5' protruding ends are filled in with deoxy-ATP and deoxy-TTP by incubation with the so-called Klenow fragment of DNA polymerase I at 25° C. so that blunt ends are produced.

The restriction endonuclease MaeI cleaves the DNA of the plasmid pCM100 between the ribosome binding site and the site where translation commences, on the one hand, and downstream of the termination signals for transcription and translation of the DNA sequence containing the gene for cyclodextrin glycosyltransferase, on the other hand. Partial cleavage of the DNA of the plasmid pCM100 is necessary because the restriction endonuclease recognizes another cleavage site within the gene for cyclodextrin glycosyltransferase.

(6) Isolation of the DNA of an expression vector.

DNA of the plasmid pJF118u which carries the ampicillin gene as marker, a tac promoter and the gene for a lac repressor is used for cloning the structural gene of cyclodextrin glycosyltransferase into an expression vector. The plasmid DNA is isolated by the method described in (2).

(7) Insertion of the structural gene coding for cyclodextrin glycosyltransferase from *Klebsiella pneumoniae* M5al into the expression vector (FIG. 1).

1 μg of the DNA of plasmid pJF118u is completely cleaved with the restriction endonuclease EcoRI at 37° C. The endonuclease is then inactivated and the 5' protruding ends are filled in with deoxy-ATP and deoxy-TTP by incubation with the so-called Klenow fragment of DNA polymerase I at 25° C. so that blunt ends are are produced. The solution of the MaeI fragment which has a length of 2,068 base-pairs and was obtained in (5) is mixed with the cleaved pJF118u vector DNA and, after addition of ATP, dithiothreitol and magnesium chloride, the mixture is incubated with the DNA ligase from the phage T4 at 17° C. for 16 hours. The resulting solution contains the recombinant DNA.

(8) Genetic transformation of *E. coli* bacteria with recombinant DNA which contains the genetic information for cyclodextrin glycosyltransferase under the control of the tac promoter.

The *E. coli* strain HB101 is cultured and prepared for transformation as described in (4). 0.2 ml of the suspension obtained as in (4) is transformed as in (4) with the solution of the recombinant DNA from stage (7). The cells are then plated out on agar plates which contain 10 g of tryptone, 5 g of yeast extract, 10 g of NaCl, 100 mg of ampicillin and 15 g of agar per liter. The plates are incubated at 37° C. After incubation for 4 hours, colonies which are resistant to ampicillin appear on the plates. They are removed and plated out in parallel on agar plates which on the one hand contain 7.1 g of $Na_2HPO_4$, 13.6 g of $KH_2PO_4$, 15 mg of $CaCl_2$, 0.25 g of $MgSO_4$, 1.6 g of $(NH_4)_2SO_4$, 5 mg of thiamine, 40 mg of proline, 40 mg of leucine, 100 mg of ampicillin, 5 g of glucose, 5 g of amylopectin azure and 15 g of starch per liter, and, on the other hand, contain the same constituents but also contain, in addition, 238 mg of isopropyl β-D-thiogalactoside as an inducer. The plates are incubated at 37° C. After incubation for 24 hours, colonies appear on the plates, some of which, on the plates which contain the inducer, are surrounded by colorless zones on the plates which are otherwise deep blue.

The latter colonies are removed, purified and isolated. Each of the colonies thus obtained is able to degrade starch after induction with isopropyl β-D-thiogalactoside and is, moreover, ampicillin-resistant.

This means that the isolated cells contain the plasmid pJF118u which carries the MaeI fragment from pCM100 having the gene for cyclodextrin glycosyltransferase, which is under the control of the tac promoter.

The plasmid is called pCM301.

While only several embodiments of the present invention have been shown and described, it is obvious that many changes and modifications may be made thereunto, without departing from the spirit and scope of the invention.

What is claimed is:

1. An isolated and purified DNA fragment consisting of the cyclodextrin glyosyltransferase structural gene of *Klebsiellapneumoniae* M5al which microorganism has been deposited as DSM 3539; and
a DNA coding region for a protein signal sequence.

2. An isolated and purified DNA fragment consisting of the cyclodextrin glycosyltransferase structural gene of *Klebsiella pneumoniae* M5al which microorganism has been deposited as DSM 3539.

3. An isolated and purified DNA fragment consisting of the cyclodextrin glycosyltransferase structural gene of *Klebsiella pneumoniae* M5al which microorganism has been deposited as DSM 3539 wherein said DNA fragment has approximately 2,068 base-pairs and is capable of being prepared by excision from the genome of the microorganism *Klebsiella pneumoniae* M5al, which microorganism produces cyclodextrin glycosyltransferase, by means of a restriction enzyme.

4. The DNA fragment according to claim 3, wherein said restriction enzyme is MaeI.

5. An isolated and purified DNA fragment consisting of the cyclodextrin glycosyltransferase structural gene and further consisting of a DNA coding region for a protein signal sequence;
wherein said DNA fragment has approximately 2,068 base-pairs and is capable of being prepared by excision from the genome of a microorganism, which produces cyclodextrin glycosyltransferase, by means of a restriction enzyme; and
wherein said microorganism is *Klebsiella pneumoniae* M5al, which microorganism has been deposited as DSM 3539.

* * * * *